United States Patent
Shafirstein et al.

(10) Patent No.: US 11,040,217 B2
(45) Date of Patent: Jun. 22, 2021

(54) SYSTEM AND METHOD FOR DELIVERING DOSE LIGHT TO TISSUE

(71) Applicant: Health Research, Inc., Buffalo, NY (US)

(72) Inventors: Gal Shafirstein, Amherst, NY (US); Brian Wrazen, Cheektowaga, NY (US); Nestor Rigual, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 15/746,699

(22) PCT Filed: Jul. 25, 2016

(86) PCT No.: PCT/US2016/043944
§ 371 (c)(1),
(2) Date: Jan. 22, 2018

(87) PCT Pub. No.: WO2017/015674
PCT Pub. Date: Jan. 26, 2017

(65) Prior Publication Data
US 2018/0207442 A1 Jul. 26, 2018

Related U.S. Application Data

(60) Provisional application No. 62/196,290, filed on Jul. 23, 2015.

(51) Int. Cl.
*A61N 5/06* (2006.01)
*A61B 18/00* (2006.01)
(Continued)

(52) U.S. Cl.
CPC .......... *A61N 5/0601* (2013.01); *A61N 5/062* (2013.01); *A61B 18/24* (2013.01);
(Continued)

(58) Field of Classification Search
CPC .......... A61B 18/24; A61B 2017/00061; A61B 2018/00642; A61B 2018/00702;
(Continued)

(56) References Cited

U.S. PATENT DOCUMENTS

| 5,330,465 A | 7/1994 | Doiron et al. |
| 6,138,046 A | 10/2000 | Dalton |

(Continued)

FOREIGN PATENT DOCUMENTS

| WO | 9214515 A1 | 9/1992 |

OTHER PUBLICATIONS

Zu, Timothy C. et al, "Prostate PDT dosimetry", Photodiagnosis and Photodynamic Therapy, Aug. 2, 2006, pp. 234-246, vol. 3, Issue 4, Elsevier, USA.

(Continued)

*Primary Examiner* — Jonathan T Kuo
(74) *Attorney, Agent, or Firm* — Hodgson Russ LLP

(57) ABSTRACT

A system and method for interstitial photodynamic light therapy (I-PDT) of a tissue. A plurality of light-transmitting catheters (LTCs) are provided and placed in the tissue according to a pre-determined treatment plan, wherein an LTC includes a first treatment fiber disposed therethrough, and an LTC includes a dosimetry fiber disposed therethrough. A dose light is provided to the tissue by way of the first treatment fiber according to the pre-determined treatment plan. Light received at the dosimetry fiber is measured using a spectrometer in operable communication with the dosimetry fiber. One or more properties of a photosensitizer in the tissue are determined. The treatment plan is modified based on the properties of the photosensitizer, and an updated dose light is provided to the tissue by way of the first treatment fiber according to the modified treatment plan.

9 Claims, 7 Drawing Sheets

(51) Int. Cl.
  *A61B 18/20*   (2006.01)
  *A61B 18/24*   (2006.01)
  *A61B 18/22*   (2006.01)
  *A61B 17/00*   (2006.01)

(52) U.S. Cl.
  CPC ............... *A61B 2017/00061* (2013.01); *A61B 2018/00642* (2013.01); *A61B 2018/00702* (2013.01); *A61B 2018/00779* (2013.01); *A61B 2018/20554* (2017.05); *A61B 2018/2261* (2013.01); *A61N 2005/063* (2013.01); *A61N 2005/0612* (2013.01); *A61N 2005/0627* (2013.01); *A61N 2005/0628* (2013.01)

(58) Field of Classification Search
  CPC ........... A61B 2018/00779; A61B 2018/20554; A61B 2018/2261; A61B 18/20–28; A61N 2005/0612; A61N 2005/0627; A61N 2005/0628; A61N 2005/063; A61N 5/0601; A61N 5/062; A61N 5/06–2005/073
  See application file for complete search history.

(56) References Cited

U.S. PATENT DOCUMENTS

| | | | |
|---|---|---|---|
| 6,811,562 B1* | 11/2004 | Pless | A61B 18/24 128/898 |
| 8,582,841 B2* | 11/2013 | Swartling | A61N 5/0601 382/128 |
| 8,767,059 B2* | 7/2014 | Endo | A61B 1/043 348/68 |
| 9,034,023 B2 | 5/2015 | Kruijt et al. | |
| 2004/0092830 A1 | 5/2004 | Scott et al. | |
| 2004/0199223 A1* | 10/2004 | Andersen | A61N 5/062 607/89 |
| 2004/0260366 A1 | 12/2004 | Svanberg et al. | |
| 2007/0282404 A1 | 12/2007 | Cottrell et al. | |
| 2008/0033339 A1 | 2/2008 | Tulip et al. | |
| 2008/0221647 A1 | 9/2008 | Chamberland et al. | |
| 2008/0249517 A1 | 10/2008 | Svanberg | |
| 2009/0043296 A1 | 2/2009 | Foster et al. | |
| 2010/0329524 A1* | 12/2010 | Swartling | A61N 5/0601 382/128 |
| 2011/0034971 A1 | 2/2011 | Svanberg et al. | |
| 2011/0074942 A1* | 3/2011 | Endo | A61B 1/043 348/68 |
| 2012/0022510 A1* | 1/2012 | Welches | A61B 18/22 606/3 |
| 2015/0057724 A1 | 2/2015 | Kuhn et al. | |

OTHER PUBLICATIONS

Trachtenberg, John et al, "Vascular-targeted photodynamic therapy (padoportin, WST09) for recurrent prostate cancer after failure of external beam radiotherapy: a study of escalating light doses", BJU International, Aug. 5, 2008, pp. 556-562, vol. 102, Issue 5, Wiley, USA.

Moore, Caroline M. et al, "Determination of optimal drug dose and light dose index to achieve minimally invasive focal ablation of localised prostate cancer using WST 11-vascular-targeted photodynamic (VTP) therapy", BJU International, May 19, 2014, pp. 888-896, vol. 116, Issue 6, Wiley, USA.

Driver, I. et al, "In vivo measurement of the optical interaction coefficients of human tumours at 630 nm", Physics in Medicine & Biology, 1991, p. 805, vol. 36, issue 6, IOPScience, United Kingdom.

Johansson, Ann et al, "Interstitial photodynamic therapy for primary prostate cancer incorporating real-time treatment dosimetry", Proceedings of Optical Methods for Tumor Treatment and Detection: Mechanisms and Techniques in Photodynamic Therapy, Feb. 27, 2007, pp. 64270O-1-64270O-11, vol. 6427, Issue 16, SPIE BiOS, San Jose, Caifornia, USA.

Krishnamurthy, Satish et al, "Optimal light dose for interstitial photodynamic therapy in treatment for malignant brain tumors", Lasers in Surgery and Medicine, Sep. 21, 2000, pp. 224-234, vol. 27, Issue 3, Wiley, USA.

Yu, Guoqiang et al, "Real-time In Situ Monitoring of Human Prostate Photodynamic Therapy with Diffuse Light", Photochemistry and Photobiology, Apr. 30, 2007, pp. 1279-1284, vol. 82, Issue 5, Wiley, USA.

Johansson, Ann et al, "Realtime light dosimetry software tools for interstitial photodynamic therapy of the human prostate", Medical Physics, Oct. 19, 2007, pp. 4309-4321, vol. 34, Issue 11, Wiley, USA.

Davidson, R. H. Sean et al, "Treatment planning and dose analysis for interstitial photodynamic therapy of prostate cancer", Physics in Medicine & Biology, Mar. 20, 2009, p. 2293, vol. 54, Issue 8, IOPScience, United Kingdom.

Huang, Zheng et al, "Effects of Pd-bacteriopheophorbide (TOOKAD)-Mediated Photodynamic Therapy on Canine Prostate Pretreated with Ionizing Radiation", Radiation research, Jun. 2004, pp. 723-731, Vo. 161, Issue 6, Radiation Research Society, USA.

Zhu, C. Timothy et al, "Determination of the distribution of light, optical properties, drug concentration, and tissue oxygenation in-vivo in human prostate during motexafin lutetium-mediated photodynamic therapy", Journal of Photochemistry and Photobiology B: Biology, Jun. 1, 2005, pp. 231-241, vol. 79, Issue 3, Elsevier, USA.

Huang, Zheng et al, "Photodynamic therapy for treatment of solid tumors-potential and technical challenges", Technology in Cancer Research & Treatment, Aug. 2008, pp. 309-320, vol. 7, Issue 4, SAGE Journals, USA.

Swartling, Johannes et al, "System for interstitial photodynamic therapy with online dosimetry: first clinical experiences of prostate cancer", Journal of Biomedical Optics, Sep. 1, 2010, pp. 058003-1-058003-9, vol. 15, Issue 5, SPIE Digtial Library, USA.

Johansson, Ann et al, "In vivo measurement of parameters of dosimetric importance during interstitial photodynamc therapy of thick skin tumors", Journal of Biomedical Optics, pp. 034029-1-034029-10, vol. 11, Issue 3, SPIE Digital Library, USA.

Tanaka, D.D.S. Hideo et al, "Interstitial photodynamic therapy with rotating and reciprocating optical fibers", Cancer, Apr. 27, 2001, pp. 1791-1796, vol. 91, Issue 9, ACS Journals, USA.

Best Medical International, Inc., Catalog 2008, Jan. 1, 2008, pp. 1-66. URL: www.bestmedicalcanada.com/pdf/BMI_Catalog.pdf.

* cited by examiner

SYSTEM AND METHOD FOR DELIVERING DOSE LIGHT TO TISSUE

CROSS-REFERENCE TO RELATED APPLICATIONS

This application claims priority to U.S. Provisional Application No. 62/196,290, filed on Jul. 23, 2015, now pending, the disclosure of which is incorporated herein by reference.

STATEMENT REGARDING FEDERALLY SPONSORED RESEARCH

This invention was made with government support under contract no. P01CA55791 awarded by the National Institutes of Health. The government has certain rights in the invention.

FIELD OF THE DISCLOSURE

The present disclosure relates to non-ionizing light therapy.

BACKGROUND OF THE DISCLOSURE

Light therapy can be used for treatment of conditions in multiple ways. For example, interstitial light therapies (ILT) involve the delivery of a therapeutic light through a fiber optic placed within a target tumor. Other therapies involve treatment with a light does at or above the tissue surface.

ILT can be combined with prior administration of light sensitive medicine (i.e., photosensitizer) that absorbs therapeutic light and interacts with surrounding tissue constituents (e.g., oxygen) to generate reactive species that can destroy the target tissue. This form of therapy is known as photodynamic therapy ("PDT"). PDT uses light (such as light provided by a laser) to activate a non-toxic drug called a photosensitizer. The process works in three ways: it destroys cancer, shuts down blood vessels that "feed" the tumor, and prompts the immune system to kill cancer cells throughout the body. It is associated with mild side effects and can be combined with standard chemotherapy and surgery, and followed with radiation therapy.

In addition or alternatively, the energy of the light can be absorbed by blood or external additives (such as metal particles) that convert the light energy into heat, to induce complete destruction of the target tissue.

In all light therapies, whether interstitial or not, whether PDT or not, it can be important that the entire tumor be illuminated with sufficient dose light in order to administer a successful treatment. To that end, proper treatment planning and control must be used.

The efficacy of photodynamic therapy is determined in part by photosensitizer availability and radiant exposure. Photofrin and other photodynamic sensitizers can be degraded by light exposure, a process called photobleaching, and this can be measured by loss of photosensitizer characteristic fluorescence. In addition, photobleaching has been shown to provide a prediction of the photodynamic dose delivered. However, quantitative measures of photosensitizer fluorescence can be complicated by changes in tissue optical properties during PDT. Accordingly, there is a need for tools to measure photosensitizer concentration and optical properties in target tissue can improve the accuracy of photodynamic dose calculation.

BRIEF SUMMARY OF THE DISCLOSURE

The present disclosure may be embodied as a method for interstitial photodynamic light therapy (I-PDT) of a tissue. A plurality of light-transmitting catheters (LTCs) are provided and placed in the tissue according to a pre-determined treatment plan, wherein at least one LTC of the plurality of LTCs includes a first treatment fiber disposed therethrough, and at least one LTC of the plurality of LTCs includes a dosimetry fiber disposed therethrough. A dose light is provided to the tissue by way of the first treatment fiber according to the pre-determined treatment plan. Light received at the dosimetry fiber is measured using a spectrometer in operable communication with the dosimetry fiber. One or more properties of a photosensitizer in the tissue are determined. The treatment plan is modified based on the properties of the photosensitizer, and an updated dose light is provided to the tissue by way of the first treatment fiber according to the modified treatment plan.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE DISCLOSURE

The present disclosure provides a method and system for light therapy treatment that enable complete and adequate illumination of an entire tumor and margins. The present techniques may be used for real-time dosimetry of therapeutic light delivered to an individual. It should be noted that, although the present disclosure is described with reference to interstitial photodynamic therapy (I-PDT), the disclosure should not be limited to I-PDT. It will be apparent to one having skill in the art in light of the disclosure that the disclosed systems and methods can be used for other modalities of non-ionizing light therapy. And such applications make up a part of the scope of this disclosure.

Figure 6:
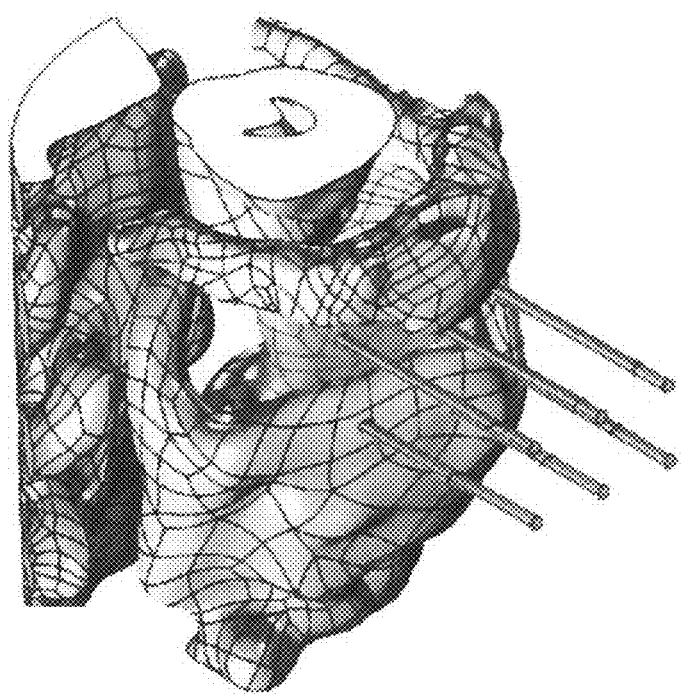
FIG. 6 depicts the geometry of FIG. 5, having an array of six LTCs inserted within the tumor, and a volumetric mesh for finite element modeling.

With references to FIG. 6, the present disclosure may be embodied as a system 10 for light therapy, such as, for example, I-PDT. Such I-PDT may be used to treat a tissue, for example, a tumor. The system 10 includes at least two light-transmitting catheters (LTCs) 14. Each catheter 14 includes a lumen 16. The catheters 14 are transparent over at least a distal end, such that treatment light can be transmitted through a wall of the catheter (i.e., from a location within the lumen 16 to a location outside of the catheter 14). The distal ends of the LTCs 14 are configured to be inserted into the tissue to be treated. In an exemplary embodiment, the lumen 16 of each LTC 14 is 1.5 mm in diameter. Other diameters can be used and will be apparent in light of the present disclosure. Embodiments of the system 10 may have 1 to 50 LTCs or more. In an exemplary embodiment, six catheters 14 are provided.

The system 10 includes a light source 20. In some embodiments, the light source 20 is a laser. The light source 20 is in operable communication with at least one treatment fiber 22. The at least one treatment fiber 22 is configured to be disposed through the lumen 16 of the catheter 14. A treatment fiber 22 is configured to transmit light from the light source 20 to a distal tip 24 of the fiber 22. In this way, therapeutic light can be introduced into the tissue to be treated. In some embodiments, more than one treatment fiber 14 is used. In the exemplary embodiment, four treatment fibers 22 are used, although embodiments may have more or less than four. The treatment fibers 22 each have a diffuse tip for emitting light within the tissue. In an exemplary embodiment, a treatment fiber 22 has a diameter of 0.98 mm. Such a treatment fiber 22 may be disposed through a lumen 16 having a diameter of, for example, 1.5 mm.

The system 10 includes a dosimetry fiber 32 configured to be disposed through the lumen 16 of an LTC 14. A dosimetry fiber 32 is configured to transmit light from a receiving end 34 of the dosimetry fiber 32 to a proximal end. A spectrometer 30 is in operable communication with the proximal end of the dosimetry fiber 32. In this way, light received at the receiving end 34 can be measured by the spectrometer 30. An exemplary dosimetry fiber 32 is 0.2 mm in diameter. Such a dosimetry fiber may be used with a catheter 14 having a lumen 16 which is, for example, 1.5 mm in diameter. It should be noted that the catheter 14, treatment fiber 22, and dosimetry fiber 32 can be configured such that both a treatment fiber 22 and a dosimetry fiber 32 may be disposed through the same catheter 14. In the exemplary embodiment, the system 10 includes eight dosimetry fibers 32, although more or less dosimetry fibers can be used. Each dosimetry fiber 32/spectrometer 30 pair may be calibrated with a light source and integrating sphere that were in turn calibrated with a National Institute of Standards and Technology (NIST) traceable standard.

Advantageously, each treatment fiber 22 and/or dosimetry fiber 32 can be used for one or more wavelengths. For example, a dosimetry fiber 32 can be used to detect a single wavelength or multiple wavelengths (for example, broadband detection). In embodiments using multiple dosimetry fibers 32 the fibers need not be used for the same wavelength as one another. The present use of a spectrometer 30 allows for broad detection of wavelengths. Similarly, treatment fibers 22 need not be used for the same wavelengths as one another. The wavelengths and ranges of wavelengths can be changed during treatment. As such, the present system 10 provides a great deal of flexibility in treating different tumors, using different drugs, etc.

Figure 1:
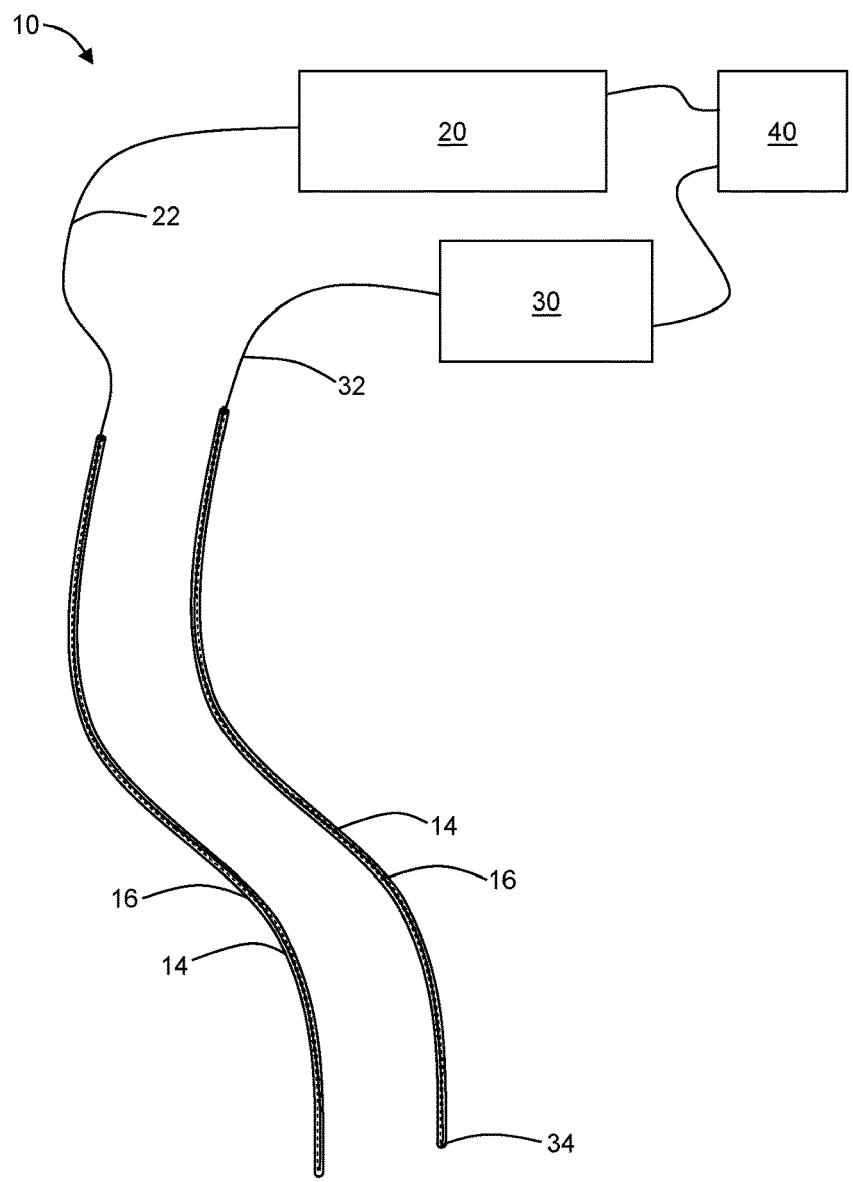
FIG. 1 is a system according to an embodiment of the present disclosure.
Figure 2:
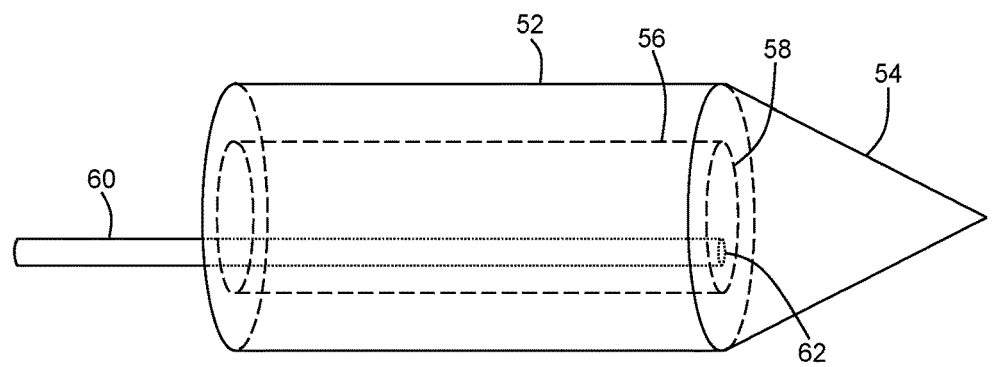
FIG. 2 is a detail view of an embodiment of a light-transmitting catheter and treatment catheter.
Figure 3:
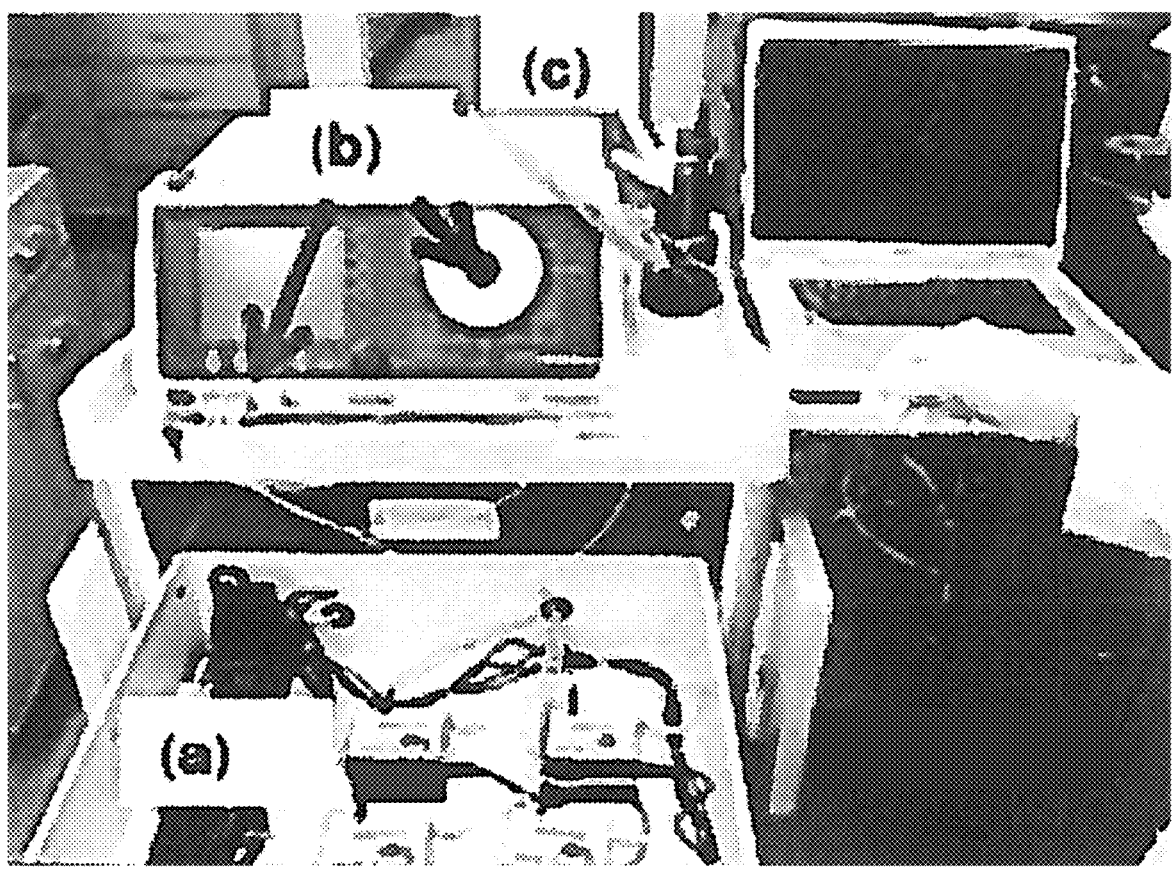
FIG. 3 is a photograph showing an exemplary system according to an embodiment of the present disclosure having (a) 8 calibrated spectrometers for measuring dose light, (b) treatment laser with delivery fibers, and (c) calibration light source and integrating sphere for calibration of dosimetry fibers.
Figure 4:
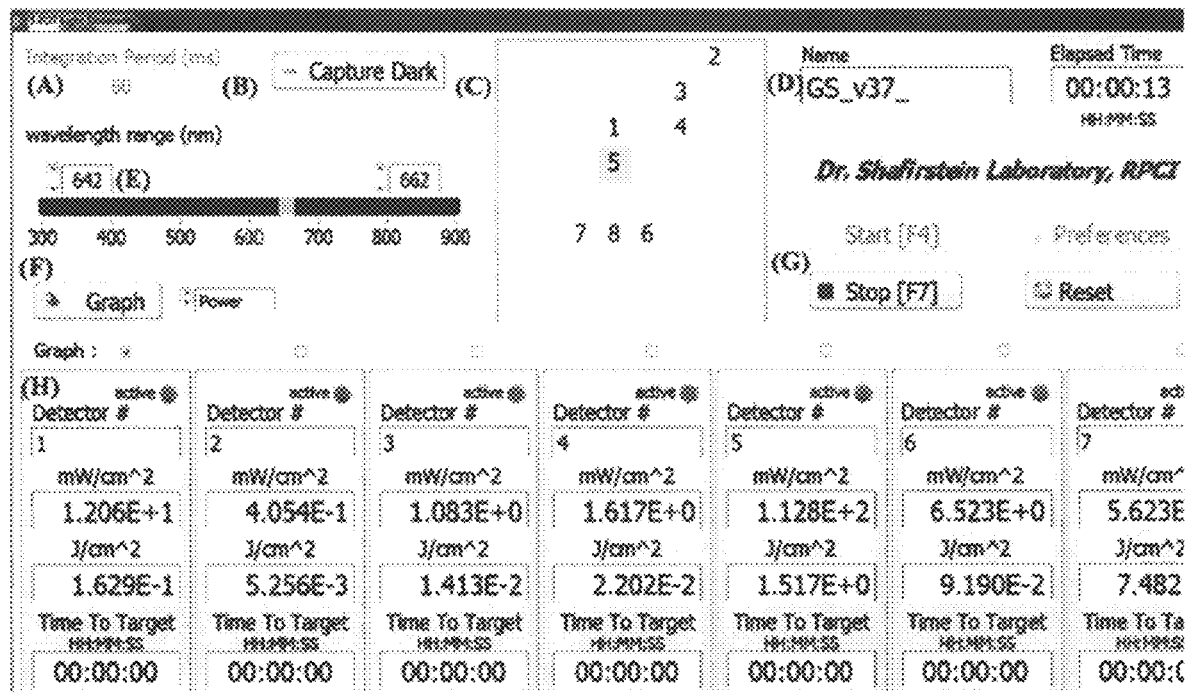
FIG. 4 depicts an exemplary screen of the controller used in the system of FIG. 3 wherein (a) is an input value for setting the integration time or acquisition time, (b) is a capture dark button to remove background light and electronic noise, (c) is a grid to present and record the relative location of the detection fibers and the laser treatment fiber(s), (d) is a file name that is assigned to each measurement, (e) is a slide bar to select the range of wavelength to be monitored according to the wavelength of the treatment light, (f) is a graph to plot the power or energy as function of wavelength detected by each detector and spectrometer, (g) is a start, stop and preferences and reset buttons, and (h) a number of columns presenting the detector number, fluence rate (mW/cm$^2$), dose light (J/cm$^2$) and time to target, which is the time that required depositing a prescribed dose light in this location.

The system 10 further comprises a controller 40. The controller 40 is configured to adjust the light delivered by the light source 20. In this way, light may be provide to a tissue from a light source 20 connected to one or more treatment fibers 22, and the light may be provided according to a treatment plan by way of control by the controller 40. The controller 40 may be, for example, a computer or any other suitable control device. The controller 40 may be programmed to control each spectrometer 30/dosimetry fiber 32 pair and record the dose light and fluence rate (W/cm$^2$). An exemplary control panel for a controller 40 is shown in FIG. 3, below. The system 10 may be designed to continuously monitor and record the delivered and transmitted dose light.

In an exemplary embodiment, a light-transmitting catheter 52 is advantageously designed with a tip 54 configured to enhance light reception, for example, a conical tip. Such a tip 54 can be used to pierce tissue in order to place the catheter 52 into a desired position. The lumen 56 may have a flat end 58 at or near the base of the conical tip 54. In such an embodiment, a therapy fiber 60 may be cleaved with a flat tip 62. In this way, the therapy fiber 60 can be disposed into the lumen 56 of the catheter 52 until the flat tip 62 abuts the flat end 58. In some embodiments, light emitted from the flat tip 62 of the catheter 52 will be diffused or otherwise spread by the conical tip 54.

Embodiments of the present disclosure may be used to provide therapeutic light according to a pre-determined treatment plan. Such treatment plans are known in the art to be determined based on models an assumptions of the tissue to be treated. The present disclosure advantageously allows for modification of the treatment plan according to light received by the dosimetry fiber(s) and measured by the corresponding spectrometer(s). For example, the optical properties of the tissue may be different than the optical properties modelled for the pre-determined treatment plan. The optical properties of the actual tissue may be determined based on the light measured by the spectrometers. These actual optical properties can then be used to recalculate/modify the treatment plan to better suit the tissue being treated. Such modification may be done in real-time. In this way, the presently disclosed techniques may provide more accurate and/or efficient dose lights (e.g., treating a tumor and its margins while minimizing the exposure of the surrounding tissue).

Figure 5:
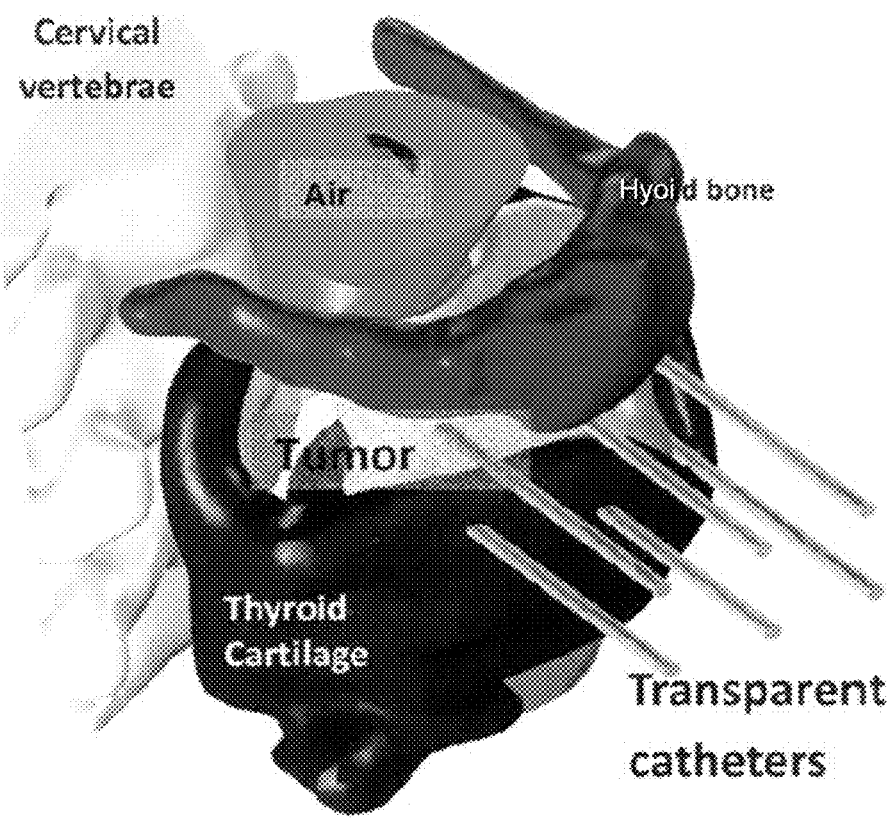
FIG. 5 depicts an I-PDT treatment schematic according to an embodiment of the present disclosure showing where treatment fibers are inserted through transparent catheters (light-transmitting catheters, or LTCs)

In an example where a tumor is to be treated (see, e.g., FIG. 5), a computed tomography (CT) or magnetic resonance (MR) image is used to obtain an image of the target tumor. Software is used to create a 3D model of the geometry of the target tissue and relevant anatomical structures (see, e.g., FIG. 6). A computer simulation is used to calculate the number and location of light transparent catheters 14 through which the treatment fibers 22 will be inserted for illuminating the tumor and margins. During therapy, a physician uses the simulation to decide where it would be best to insert catheters 14. Prior to insertion, the physician utilizes standard medical imaging (typically ultrasound) to image the sites of where the LTCs will be inserted, to assure patient's safety. Insertion may be accomplished using, for example, real-time image guidance using ultrasound or CT, or insertion can be guided with a robotic arm that will register the location in 3-D with reference to the images simulation, model, and/or images described above.

Once the LTCs 14 are in place, ultrasound, MRI, or CT can be used to measure the actual location of the fibers and each LTC 14 is marked with a number. A target dose light is prescribed for each location. The target light does is the amount of light that should be delivered from each treatment fiber 22 at a specific LTC 14. The target dose light is based on prior clinical data or prior work in pre-clinical settings that showed promising results in an effective drug activation and response to I-PDT or ILT.

Treatment fibers 22, dosimetry fibers 32, or both are placed in the various marked LTCs 14. The number of LTCs can be 1-50 or more, and the number of dosimetry fibers may be 1-8 (but can be as high as 24 or more). In some embodiments, more dosimetry fibers than treatment fibers are placed in the LTC array. In some embodiments, the diameter of our dosimetry fibers is 0.2 mm, the diameter of the treatment fibers is 0.98 mm, and the inside diameter of the LTCs is about 1.5 mm; as such, a dosimetry fiber and a treatment fiber may be placed in the same LTC. This combination allows measurement of the light output from treatment fibers during therapy, and the light delivery to nearby LTCs that have no treatment fibers.

Measuring the dose light from the treatment fibers and at a distance is not trivial, because the dose light next to the treatment fiber is much higher than the dose as measured from, for example, 10 mm away. Obtaining both dosage measurements (near and far) at the same time is beneficial, because it allows for calculating optical properties in real time. Embodiments of the present disclosure allow measurement of very high and relatively low dose lights at the same time by modifying the acquisition time of a measurement in order to record a wide range of dose lights.

Figure 7:
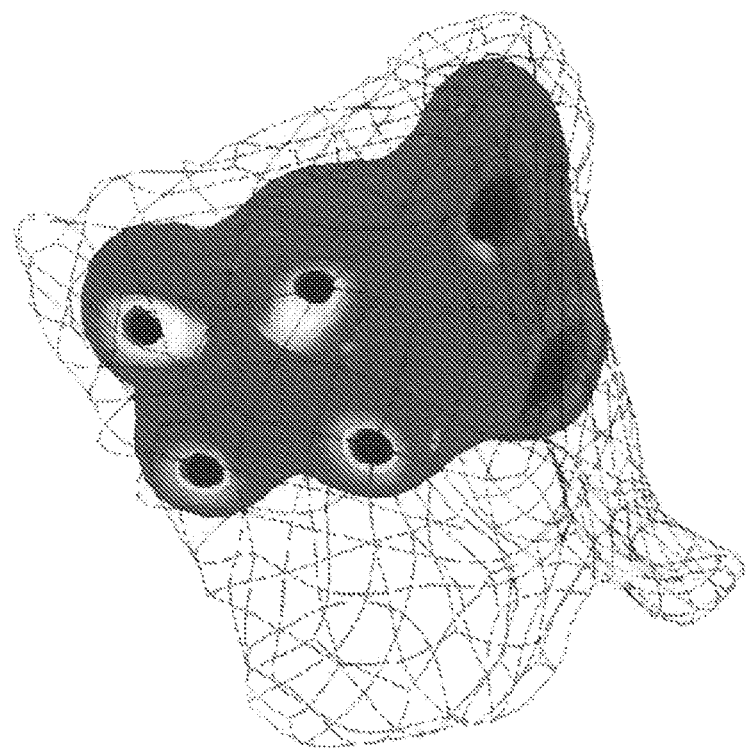
FIG. 7 is the calculated dose light (J/cm$^2$) distribution within the target tumor of FIGS. 5 and 6.
Figure 8:
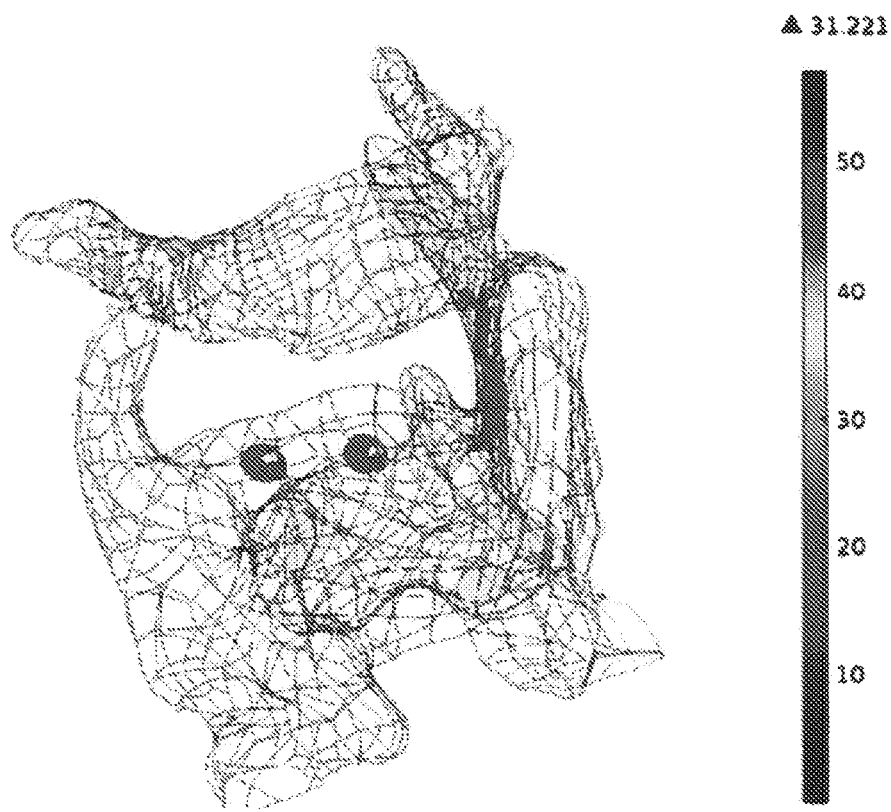
FIG. 8 is the calculated dose light distribution within the non-tumor tissue, suggesting that only a small portion of the non-tumor tissue will be exposed to a dose light that can induce I-PDT (20 J/cm$^2$ or greater)

The real-time measurement data may then be used to calculate the optical properties within the treated tumor. In some embodiments, a look-up table may be provided for determining relevant optical properties from measured values of light dosage. These optical properties can then be used to recalculate the light distribution within the target tumor—thereby modifying the treatment plan. As such, regions of the tumor and/or surrounding tissue can be identified as being over treated or under treated (see FIGS. 6-8).

In a simulation of the exemplary method, therapy required 1-1.5 min, whereas a typical therapy takes at least 20-30 minutes. The presently disclosed system is suitable for any drug and light wavelength in the range of, for example, 400-1200 nm. The presently disclosed systems and methods are suitable for use on heterogonous tumors such as, for example, head or neck cancer.

Figure 13:
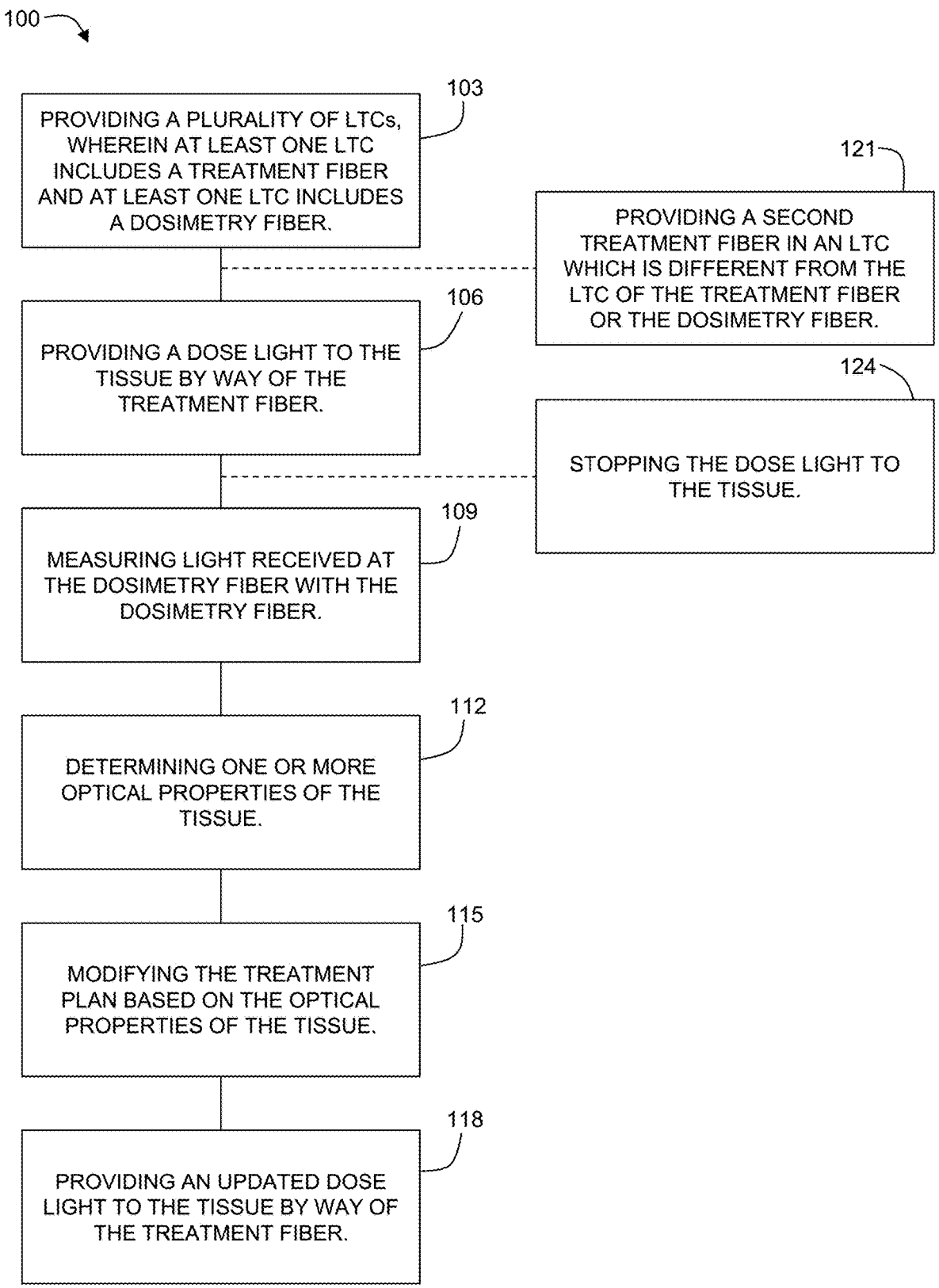
FIG. 13 is a chart of a method according to another embodiment of the present disclosure.

In another aspect, the present disclosure is embodied as a method 100 for interstitial photodynamic light therapy (I-PDT) of a tissue (see, e.g., FIG. 13). The method 100 includes providing 103 a plurality of light-transmitting catheters (LTCs) placed in the tissue according to a pre-determined treatment plan. At least one LTC of the plurality of LTCs includes a first I-PDT treatment fiber disposed therethrough. At least one LTC of the plurality of LTCs includes a dosimetry fiber disposed therethrough. A dose light is provided 106 to the tissue by way of the treatment fiber according to the pre-determined treatment plan (as discussed above).

Light received at the dosimetry fiber is measured 109 using a spectrometer in operable communication with the dosimetry fiber. The light measured 109 at the dosimetry fiber may be a measurement light. The measurement light may be a different wavelength from that of the dose light. In some embodiments, the measurement light is the same wavelength as light emitted by a photosensitizer when the photosensitizer is excited. For example, when Photofrin is used, the dose light may be at 630 nm and the measurement light may be at 690 nm. In some embodiments, the measurement light is provided by a second treatment fiber. In such cases, the method 100 includes providing 121 a second treatment fiber in an LTC which is different from the LTC of the first treatment fiber. The dose light may be stopped 124 during a time of light measurement 109 at the dosimetry fiber.

One or more properties of a photosensitizer in the tissue are determined 112 based on the light measured 109 at the dosimetry fiber. For example, the rate and/or response of the photosensitizer may be determined 112. The treatment plan is modified 115 based on the determined 112 properties of the photosensitizer. An updated dose light is provided 118 to the tissue by way of the treatment fiber(s) according to the modified treatment plan.

EXEMPLARY EMBODIMENTS

Figure 9:
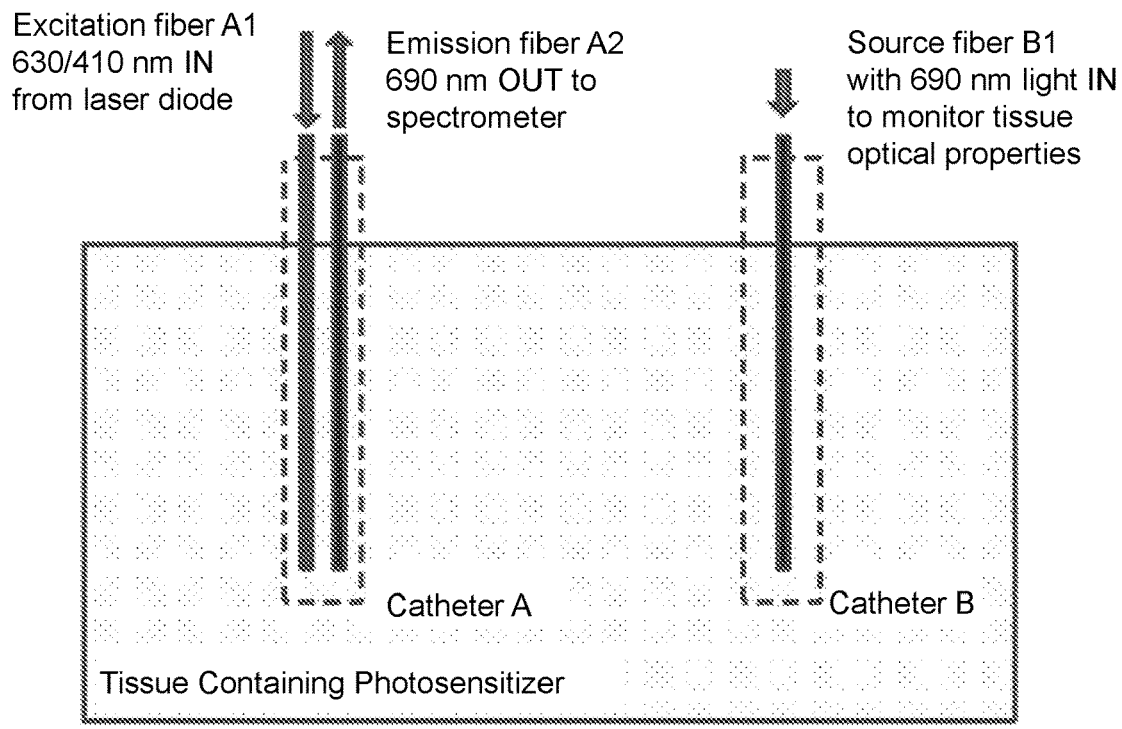
FIG. 9 depicts an exemplary embodiment of the present disclosure.

In the exemplary embodiment depicted in FIG. 9, catheter A contains two optical fibers, A1 and A2. The excitation fiber A1 (i.e., the treatment fiber) delivers light to excite the photosensitizer to generate singlet oxygen for PDT of the target tissue. For example, for Photofrin, the delivered light is at 630 nm. This same light also excites characteristic fluorescence emission of Photofrin at 690 nm. The detection fiber A2 (i.e., the dosimetry fiber) is attached to a spectrometer to measure fluorescence emission wavelength and intensity. Alternatively, fiber A1 can deliver 405 nm light to provide a much stronger fluorescence signal because: (i) Photofrin absorbs light at 410 nm~15-fold more than at 630 nm; and (ii) excitation at 405 nm light will result in two emission bands (630 nm and 690 nm).

In the exemplary embodiment, catheter B contains a single fiber. Source fiber B1 emits light (for Photofrin, 690 nm) that travels through tissue and is collected by detection fiber A2 in catheter A. The intensity of the light collected by fiber A2 is used to monitor changes in tissue optical properties during the course of therapy. To do this, the 630-nm light is momentarily turned off so that only 690-nm light from source B1, and not Photofrin-characteristic fluorescence emission at 690 nm, will be collected.

Proof of principle for fluorescence detection of Photofrin was demonstrated in solution, containing phosphate buffered saline, 10% fetal calf serum and 5 µg/mL Photofrin. 12 mL of solution was placed in a black, light-tight Delrin well. The well-cover included ports to allow insertion of closed-end, 15G polycarbonate Flexi-Needle needle guide catheters into the well.

Figure 10:
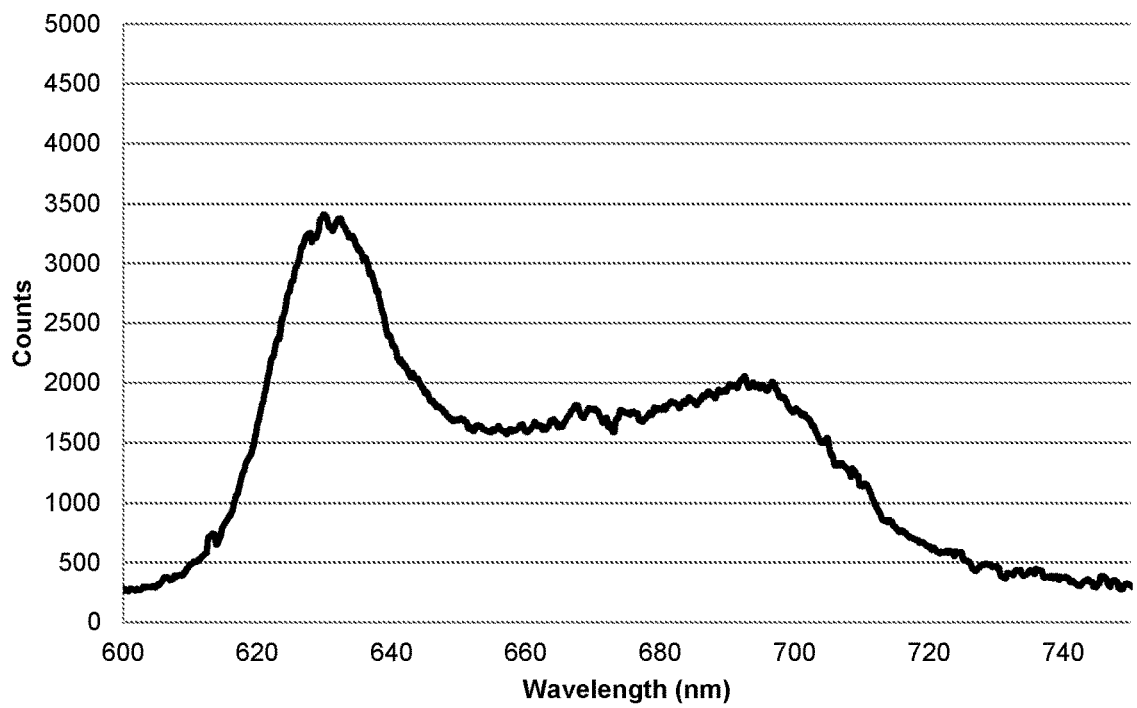
FIG. 10 is a graph showing Photofrin fluorescence excited at 410 nm in liquid phantom containing fetal calf serum.

Excitation fiber A1 was a Medlight RD20 fiber-optic with a 2-cm length cylindrical diffuser; this fiber was attached to either a Modulight 630-nm laser diode or Powertech Inc. 410-nm laser diode. Detection fiber A2 was a 200 μm, flat-cut, 0.22 NA quartz fiber-optic; this fiber was attached to an Ocean Optics USB200+ spectrometer. Fluorescence $\lambda_{ex}$=410 nm) from Photofrin in solution is shown in FIG. 10.

Figure 11:
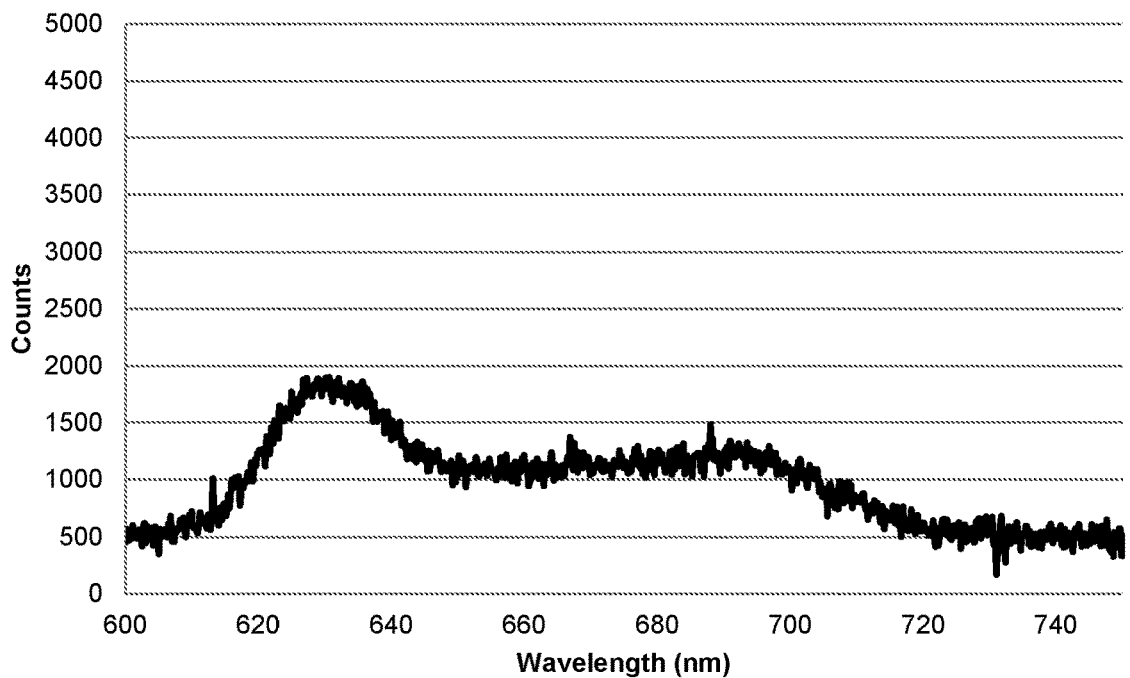
FIG. 11 is a graph showing Photofrin fluorescence excited at 410 nm in liquid optical phantom containing 2.6 μM hemoglobin and 1 μm microspheres; μs'=5.0 cm$^{-1}$)
Figure 12:
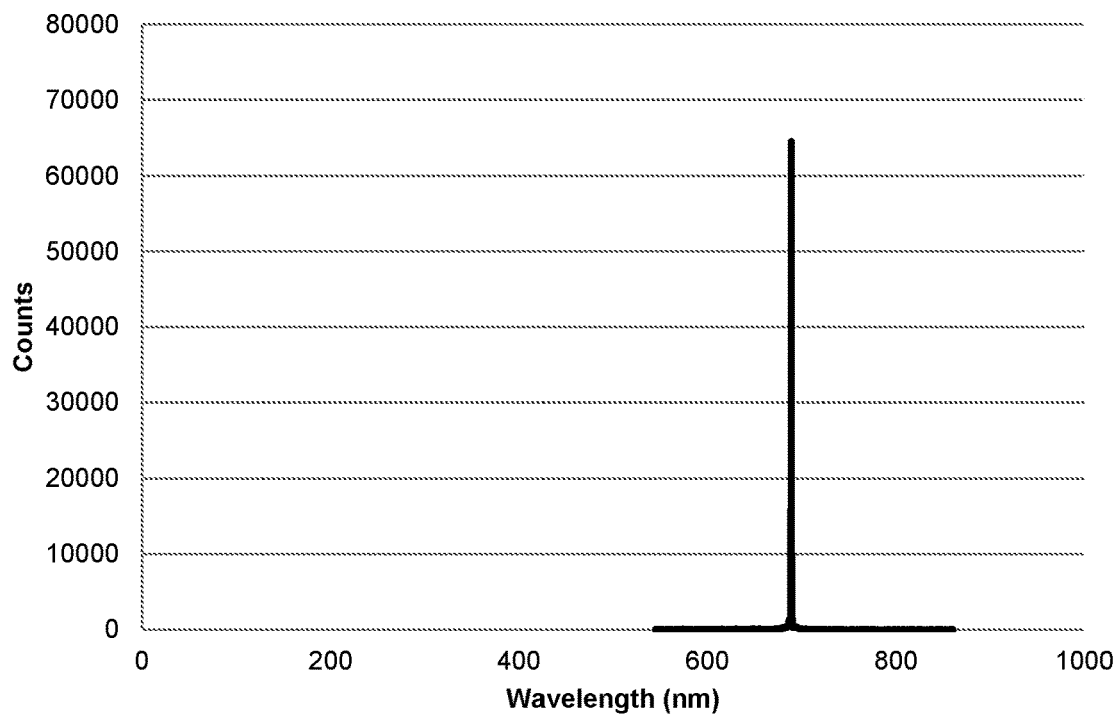
FIG. 12 is a graph showing the signal detected across 0.44 cm of the liquid optical phantom of FIG. 11, where the source light was at 690 nm.

In a subsequent study, a more robust liquid optical phantom was prepared from a mixture of microspheres and hemoglobin (Hb) (experimental conditions are shown in FIGS. 11 and 12). FIG. 11 shows the detection of backscattered Photofrin fluorescence using 410 nm (fiber A1) and detection fiber A2 placed in catheter A. FIG. 12 shows the detection of 690 nm light from source fiber B1 to detection fiber A2 through 5 mm of liquid optical phantom.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

We claim:

1. A method for interstitial photodynamic light therapy (I-PDT) of a tissue, comprising:
  providing a plurality of light-transmitting catheters (LTCs), each of the plurality of LTCs comprising:
  an elongated light transmissible flexible hollow cylinder having a distal end and a flat end positioned at the distal end;
  a light transmissible conical tip positioned at the flat end, wherein the light transmissible conical tip is adapted to pierce the tissue and is further adapted to diffuse a dose light and enhance reception of a measurement light; and
  any of at least one of a treatment fiber and a dosimetry fiber disposed within the elongated light transmissible flexible hollow cylinder and in operable communication with the flat end;
  piercing the tissue with the light transmissible conical tip of the plurality of LTCs;
  placing the distal end of the plurality of LTCs in the tissue according to a pre-determined treatment plan;
  delivering the dose light to the tissue by way of the light transmissible conical tip of a first of the at least one treatment fiber according to the pre-determined treatment plan;
  receiving the measurement light by way of the light transmissible conical tip of a first of the at least one dosimetry fiber; and
  measuring the measurement light using a spectrometer in operable communication with the dosimetry fiber.

2. The method of claim 1, further comprising:
  determining one or more properties of a photosensitizer in the tissue;
  modifying the pre-treatment plan based on the properties of the photosensitizer and producing a modified treatment plan; and
  providing an updated dose light to the tissue by way of the first of at least one treatment fiber according to the modified treatment plan.

3. The method of claim 2, wherein the delivering of the dose light is stopped during a time of the measuring the measurement light at the dosimetry fiber.

4. The method of claim 3, wherein the dose light has a wavelength which is different from a wavelength of the measurement light.

5. The method of claim 4, wherein the wavelength of the measurement light is the same as a light emitted by the photosensitizer.

6. The method of claim 5, wherein a second treatment fiber is disposed in an LTC of the plurality of LTCs which is different from the LTC of the first treatment fiber;
  and wherein the measurement light is provided at the second treatment fiber.

7. The method of claim 4, wherein a second treatment fiber is disposed in an LTC of the plurality of LTCs which is different from the LTC of the first treatment fiber;
  and wherein the measurement light is provided at the second treatment fiber.

8. The method of claim 3, wherein a second of the at least one treatment fiber is disposed in an LTC of the plurality of LTCs which is different from the LTC of the first treatment fiber; and wherein the measurement light is provided at the second of the at least one treatment fiber.

9. The method of claim 2, wherein the one or more properties of the photosensitizer includes a rate and/or a response of the photosensitizer.

* * * * *